United States Patent [19]

Mulhollan et al.

[11] Patent Number: 4,621,640

[45] Date of Patent: Nov. 11, 1986

[54] MECHANICAL NEEDLE CARRIER AND METHOD FOR ITS USE

[76] Inventors: James S. Mulhollan, 3401 Foxcroft Rd., Little Rock, Ark. 72207; Lionel Starr, 8806 Patricia Lynn, Sherwood, Ark. 72116

[21] Appl. No.: 569,448

[22] Filed: Jan. 9, 1984

[51] Int. Cl.⁴ .............................................. A61B 17/06
[52] U.S. Cl. .................. 128/340; 128/334 R; 128/339; 112/169; 112/222; 223/102; 223/104
[58] Field of Search ............... 128/334 R, 339, 340; 112/169, 222; 223/102, 104

[56] References Cited

U.S. PATENT DOCUMENTS

| | | | |
|---|---|---|---|
| 1,449,068 | 3/1923 | Snyder | 223/102 |
| 2,327,353 | 8/1943 | Karle | 128/340 |
| 2,336,690 | 12/1943 | Karle | 128/340 |
| 2,348,218 | 5/1944 | Karle | 128/340 |
| 2,393,910 | 1/1946 | Karle | 128/340 |
| 2,646,045 | 7/1953 | Preestley | 128/340 |
| 2,737,954 | 3/1956 | Knapp | 128/340 |
| 3,073,311 | 1/1963 | Tibbs et al. | 128/340 |
| 3,168,097 | 2/1965 | Dormia | 112/169 |
| 3,878,848 | 4/1975 | Hilbert | 128/340 |
| 4,414,908 | 11/1983 | Eguchi et al. | 112/222 |
| 4,417,532 | 11/1983 | Yasukata | 128/334 R |
| 4,440,171 | 4/1984 | Nomoto et al. | 128/334 R |
| 4,471,781 | 9/1984 | Di Giovanni et al. | 128/339 |
| 4,491,135 | 1/1985 | Klein | 128/340 |
| 4,493,323 | 1/1985 | Albright et al. | 128/340 |

OTHER PUBLICATIONS

Singer Surgical Stitching Instrument (pp. 1–7), Singer Sewing Machine Company, 1942.

*Primary Examiner*—Andrew H. Metz
*Assistant Examiner*—Helane Myers
*Attorney, Agent, or Firm*—Hill, Van Santen, Steadman & Simpson

[57] ABSTRACT

A mechanical needle carrier is provided which can grasp and carry a surgical needle through a cannula, position the needle and set a stitch at the remote location and then release the needle and be withdrawn from the cannula.

13 Claims, 9 Drawing Figures

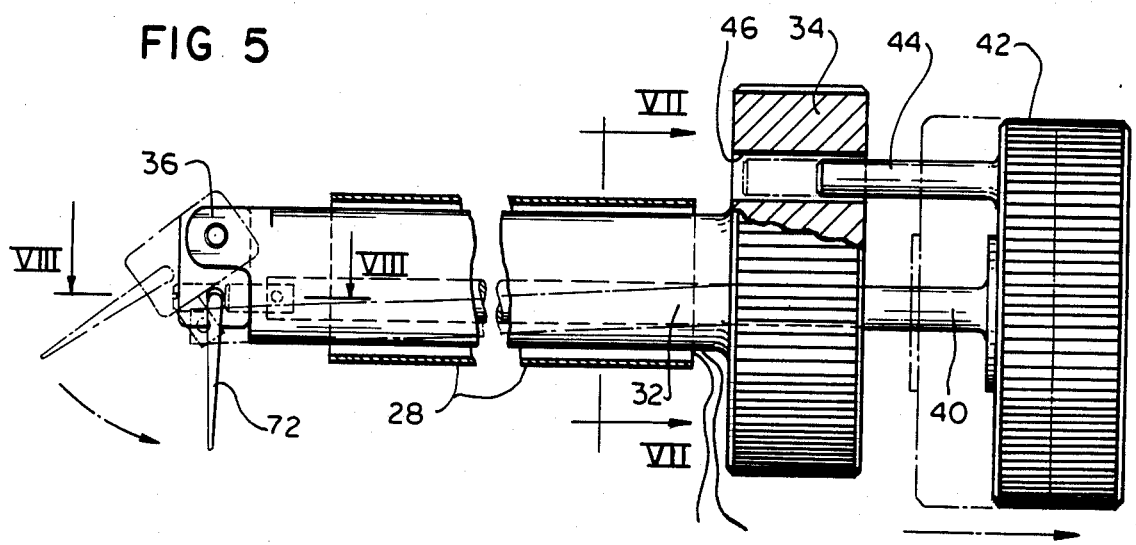
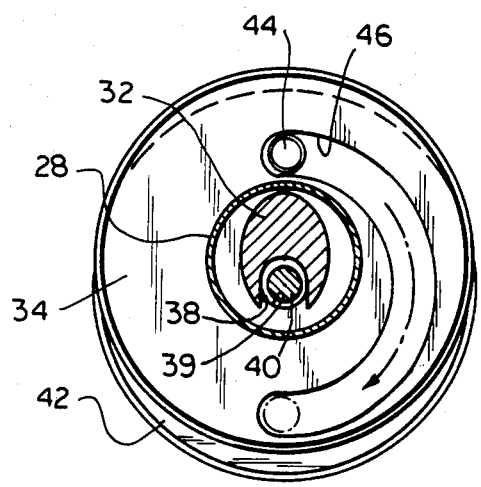
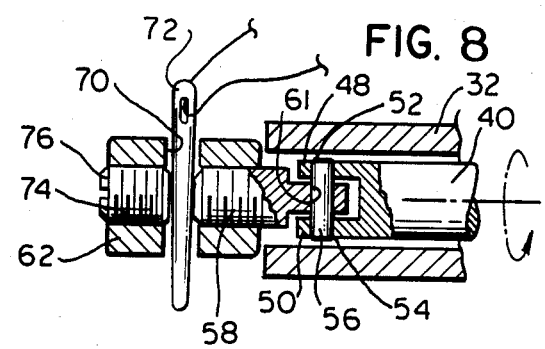
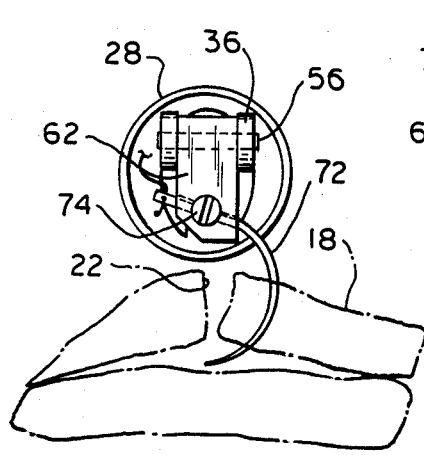
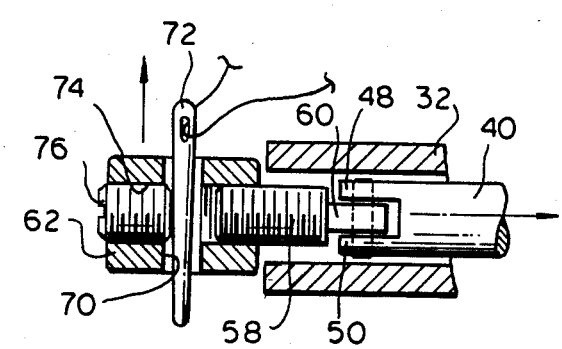

MECHANICAL NEEDLE CARRIER AND METHOD FOR ITS USE

BACKGROUND OF THE INVENTION

1. Field of the Invention

This invention relates to surgical instruments and more particularly to a device for carrying, gripping and manipulating a needle for placing sutures within a body of tissue or cartilage such as the body of a human being or of an animal.

2. Description of the Prior Art

Many surgical procedures are currently being performed where it is necessary to make a large opening to expose the area of, for instance, a human body that requires surgical repair. This is true even though there are instruments available which allow the viewing of certain areas which have limited accessibility. For example, arthroscopes are available to permit viewing of a human knee joint through a puncture wound without exposing the entire joint of the knee by cutting through the skin in that area.

These viewing instruments can be used to detect, among other things, surgically repairable tears within the cartilage of the knee. Shaving instruments exist which allow parts of the damaged cartilage to be shaved off and removed from the kee joint through a cannula or tube without requiring that the knee be opened. However, prior to this time it has been necessary to open the knee to sew the tear in the cartilage.

When an area of the body is cut into to expose an interior portion thereof, that process involves some morbidity which increases as more muscle layers, ligaments and other tissues are cut and separated. This morbidity, or time and discomfort associated with recovery and change of complications, would be greatly reduced if the required surgery were performed without making a large incision, cutting and separating various tissues, and exposing a large portion of the interior of the body.

SUMMARY OF THE INVENTION

The invention provides for a device and method of performing surgical repair requiring stitches on areas of the interior of the body having limited access through a cannula. This is done percutaneously, or through a puncture wound in the skin, without requiring a large incision for exposing the interior of the body. The device of the present invention comprises a mechanical needle carrier which is small enough to be inserted in a cannula yet sturdy enough to provide transmission of enough torque to set a surgical needle in relatively tough tissue. The device is operable to change the position of the carried needle by 90 degrees after the needle is in a cavity in the body proximate to the area to be sewn. Also, the needle carrier has the ability to grasp the needle very securely during passage through the cannula. Rotation of the grasped needle is prevented while it is pushed through the tissue being sutured. The needle carrier further provides for firm and certain release of the needle once it is placed. Once the needle has been released, the device can be removed and reinserted for placement of additional stitches.

Thus, the present invention provides the advantage of being able to make repairs requiring stitches within the interior of a body in a relatively inaccessible area through a puncture wound without making a large incision.

BRIEF DESCRIPTION OF THE DRAWINGS

FIG. 5 is a partial top view of the needle carrier device showing movement of the head portion.

FIG. 6 is an end view of the needle carrier device and showing the needle setting a stitch.

FIG. 7 is a sectional view of the body of the needle carrier taken generally along the line VII—VII of FIG. 5.

FIG. 8 is a partial side sectional view of the gripping portion of the needle carrier in the grip position taken generally along the line VIII—VIII of FIG. 5.

FIG. 9 is a partial side sectional view of the gripping portion shown in FIG. 8 in the release position.

DESCRIPTION OF THE PREFERRED EMBODIMENTS

Figure 1:
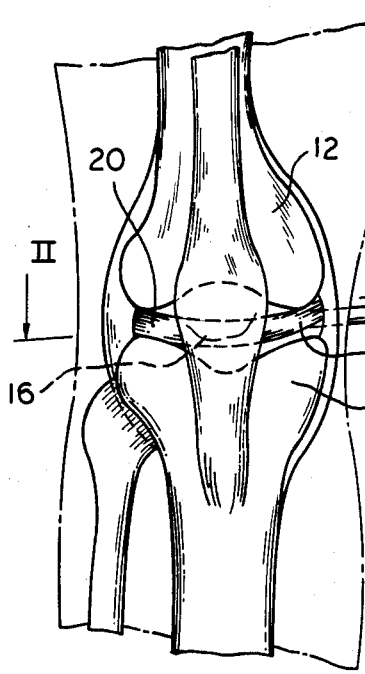
FIG. 1 is a front view of the environment of a human knee showing the joint structure in full lines and the outline of a leg phantom and showing the mechanical needle carrier device in place.
Figure 2:
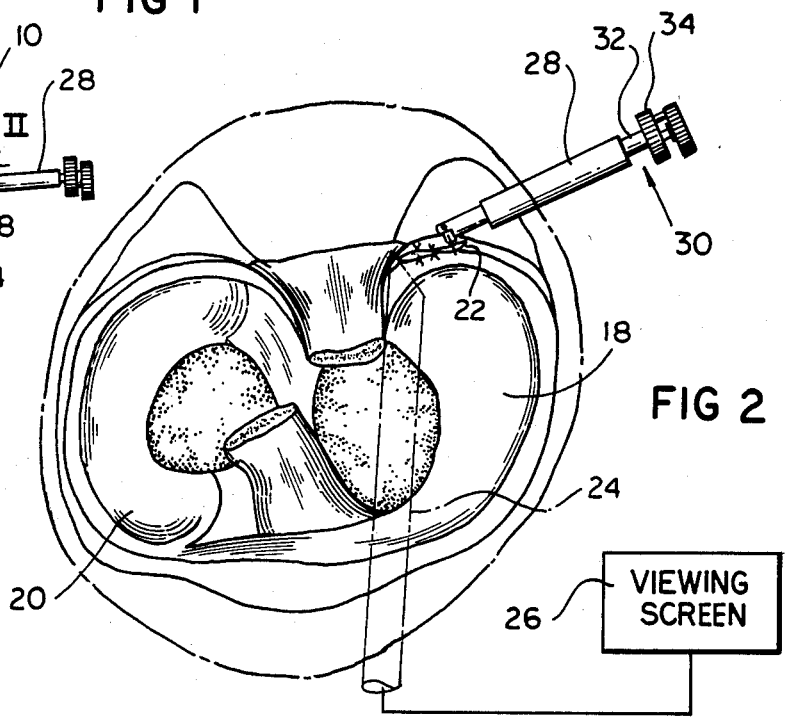
FIG. 2 is a top sectional view though the knee showing the placement of the mechanical needle carier device in operation, taken generally along the line II—II of FIG. 1.

Although the principles of the present invention are applicable to any device suitable in surgical procedures whether performed on humans or animals, a particular utility is effected in human knee surgery where the problems of surgery are particularly acute. Accordingly, as an illustrative exemplification of our invention in FIG. 1 there is shown a human knee joint generally at 10 which provides an environment in which the present invention is especially useful. Within the knee joint 10 there is shown the femur bone 12, the tibia bone 14, the patella or knee cap 16 and the medial meniscus 18 and lateral meniscus 20. The menisci 18, 20 are cartilage structures in contact with both the femur 12 and tibia 14. As seen in FIG. 2, the menisci are crescent shaped with a central opening area. Certain injuries to the knee cause tears to the menisci such as that shown in 22 in FIG. 2.

Arthroscopes are available which have a light and optics probe, as shown at 24, which can be inserted through a puncture wound for viewing the interior portion of the knee joint 10 through a viewing lens or screen shown schematically at 26 (FIG. 2). The arthroscope permits the physician or surgeon to see the tear 22 without surgically opening the knee to expose that portion of the joint.

A hollow cannula or tube 28 can be inserted through the skin around the knee joint to a position proximate to the tear 22 in the meniscus 18. Various instruments can be inserted through this cannula 28 to perform various surgical tasks. The present invention provides for an instrument which can be inserted through this cannula 28 to set a stitch in the meniscus so that the tear 22 can be sewn shut to assist in the healing process without opening the knee to expose this portion of the knee joint. Such a procedure is greatly advantageous over previous methods of knee surgery in that healing time is drastically reduced to days instead of weeks. Rehabilitation of the knee joint after surgery is not required anywhere near the degree it has heretofore been required.

A mechnanical needle carrier 30 is shown in each of the figures and is comprised of a rod member 32 having a knurled flange 34 at one end and a pair of extending ears 36 forming a yoke at an opposite end thereof. The rod 32 has an outer diameter sufficiently lesser than the inner diameter of the cannula bore to afford a clearance to allow it to move loosely in the cannula 28. A typical rod diameter would be about 5 mm. A channel 38 extends the length of the rod 32 and includes a hole 39 through the flange 34.

A second, smaller diameter rod 40 extends through the flange 34 and telescopically along the length of the channel 38. An enlarged knurled end 42 is provided on the second rod 40 which is positioned adjacent to the flange 34 of the first rod 21. A post 44 projects from the knurled end 42 in the same direction as the second rod, but spaced therefrom, which projects into and is received in a semi-circular slot 46 provided in the flange 34 of the first rod 32. Thus limited rotation of the second rod 40 relative to the first rod 32 can be accomodated. Further, limited axial movement of second rod 40 relative to the first rod 32 can be accomodated while still allowing the post 44 to be engaged in the slot 46. The second rod 40, at an end opposite the knurled end 42 is provided with a pair of extending ears 48, 50, best seen in FIGS. 8 and 9, which each have a hole 52, 54 therethrough for receiving a pivot pin 56. A threaded stud 58 has a projecting post 60 with a passage 62 therethrough which receives the pivot pin 56. Thus, the threaded stud 58 is pivotally attached to the end of the second rod 40.

A needle carrying head 62 has a first cylindrical passage 64 therethrough for receiving a pivot pin 66 which extends into holes 68 in the ears 36 of the first rod 32. In this manner, the needle carrying head 62 is pivotally attached at an axis of rotation to the first rod 32.

The needle carryiing head 62 has a second passage 70 passing therethrough for receiving a surgical needle 72. A third passage 74 intersects the second passage 72 and has a threaded interior diameter. A set screw 76 is threaded into one end of the passage 74 to engage one side of the needle 72 carried within the passage 70 and the threaded stud 58 is threaded into a second end of the passage 74 to engage an opposite side of the needle 72, as shown in FIG. 8. In this manner, the needle 72 is securely clamped or gripped in place.

Figure 3:
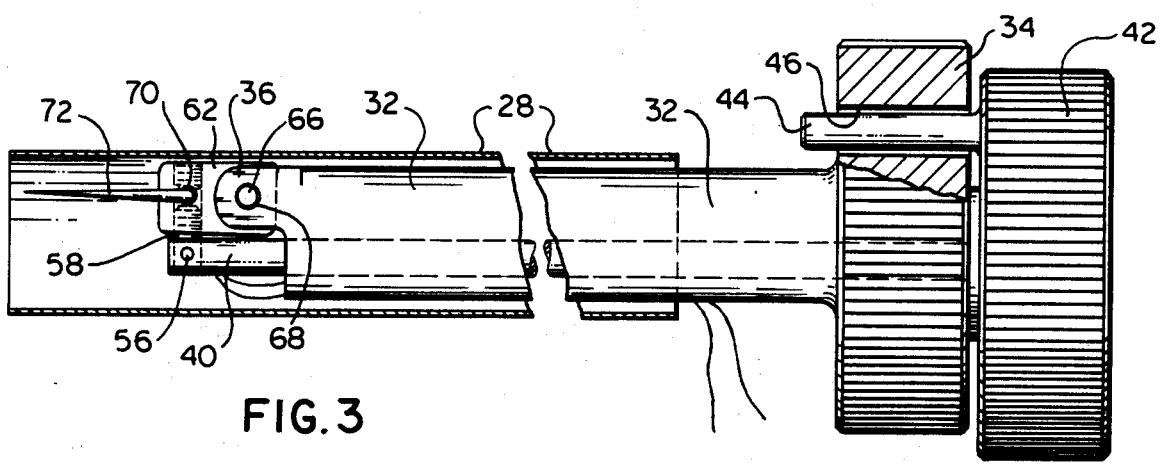
FIG. 3 is a detailed cross sectional view of a portion of the needle carrier device with needle inside a cannula.
Figure 4:
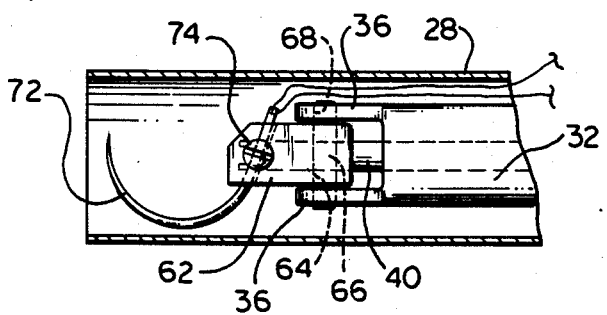
FIG. 4 is a top cross sectional view of the device shown in FIG. 3.

To insert the needle carrier 30 through the cannula 28, rod 40 is moved axially relative to rod 32 by pushing the two knurled ends 42, 34 together. This causes the needle carrier head 62 to pivot on pivot pin 66 through the linkage of stud 58 so that the needle is pointing forward as shown in FIG. 3. When the rods 32, 40 are in this position, second rod 40 is prevented from rotating relative to the first rod 32. Once the needle and needle head are within the cavity within the knee as shown in FIG. 2, the knurled end 42 is pulled away from the knurled flange 34 as shown in FIG. 5. This causes the needle carrying head 62 to pivot about pin 66 until the needle 72 is at right angles to the rod 32. With the needle in such an orientation, it can then be manipulated or rotated in a second plane or about a second axis rotation to set a stitch in the injured tissue as shown in FIG. 6. Once the needle has been set in the tissue, it is necessary that the needle be released by the needle carrier 30. To accomplish this, the knurled end 42 is rotated in a counter clock-wise direction relative to the knurled flange 34 thus turning rod 40 and the associated threaded stud 58. This allows the stud 58 to back off from the needle 72 as is shown in FIG. 9 which thereby releases the gripping action on the needle.

By twisting the knurled flange 34, the needle carrier head 62 can be moved to disengage with the needle 72. The two rods are then moved axially relative to one another by pushing the knurled end 42 towards the knurled flange 34 returning the needle carrying head 62 to its insertion position, allowing the needle carrier 30 to be removed from the cannula. Other instruments can then be inserted into the cannula to pull the needle through and to set and tie knots.

In other words, this invention provides the structure and method for suturing in a restricted field of surgical operation from an area of manipulation remote from the field which includes a first member such as a surgical needle supported for rotation on a first axis of rotation intersecting the field and the area. Means including a second member which is continuously axially adjstable relative to the first member along the first axis is provided with means journaling the first member for rotation on a second axis of rotation perpendicular to the first axis of rotation, and actuating means between the first and second members for effecting rotation on the second axis in response to relative axial adjustments of the second member.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A mechanical needle carrier capable of grasping and releasing a surgical needle comprising:
   means for securely grasping said needle,
   means for guiding said surgical needle to a specific area, means for positioning said needle in a desired orientation by rotation about a first axis,
   means for directing said needle to a desired location for setting a stitch by pivoting said needle about a second axis, perpendicular to said first axis,
   means for releasing said needle after said stitch is set, and
   means for retracting said needle carrier from said specific area,
   whereby, after said grasped needle is guided to said specific area it is positioned by rotation about said first axis and stitches are set by rotation of said needle about said second axis, then said needle is released from said carrier and the carrier is retracted from said specific area.

2. A mechanical needle carrier according to claim 1 wherein said means for guiding the surgical needle includes an access tube through which said carrier passes to said specific area.

3. The device of claim 2, wherein said means for guiding said needle through said tube comprises a needle carrying head, pivotable about said first axis, carried on an end of a cylinderical rod member having releasable gripping means to securely hold said needle.

4. The device of claim 2 wherein said means for securely grasping and said means for releasing said needle comprises opposed and selectively movable members engageable on opposite sides of said needle.

5. The device of claim 3 wherein said means for retracting said needle carrier comprises means for pivoting said head about said first axis to return said head to its original orientation.

6. A mechanical needle holder comprising:
a first rod member having
a knurled flange on a first end,
a pair of extending ears forming a yoke at a second end,
a channel extending along a first axis between said ends and including a passage through said knurled flange,
a second rod member carried in and being axially movable and rotatable in said channel an extending through said passage having an enlarged knurled first end adjacent said knurled flange, a pair of extending ears forming a yoke at a second end,
a needle carrying head member connected to said yoke of said first rod member to pivot about a second axis, perpendicular to said first axis, and having a passage for receiving a surgical needle, and
linkage means pivotally connected to said yoke of said second rod member and connected to said head member and including a portion engagable with said needle upon rotation of said second rod member,
whereby, axial movement of said second rod member relative to said first rod member causes rotation of said head member about said second axis through said linkage means and rotational movement of said second rod member relative to said first rod member causes engagement and disengagement of a portion of said linkage means with said needle.

7. The device of claim 6 including means associated with said first and second rod members to limit the amount of relative rotation about said first axis between said members.

8. A system for setting a surgical stitch in a location of limited accessibility comprising:
a cannula which can be positioned with a first end adjacent said location of limited accessibility and with a second end exposed to an area of accessibility,
a needle carrier insertable through said second end of said cannula and having means for securely grasping and carrying a surgical needle to said location of limited accessibility,
means for positioning said needle by rotation about a first axis from outside the area of limited accessibility after said needle has been carried to said location of limited accessibility,
means for directing said needle to an area requiring a stitch from outside the area of limited accessibility by rotating said needle about a second axis, perpendicular to said first axis to set the stitch,
means for releasing said needle, and
means for retracting said needle carrier from said cannula,
whereby, after said stitch has been set, said needle is released from said carrier and said carrier is removed from said cannula.

9. A method of setting a surgical stitch in torn or cut tissue in a relatively inaccessible area within the body of a patient comprising the steps:
establishing visual contact with said area to be stitched,
inserting a cannula into said area to be stitched,
guiding a surgical needle and suture through said cannula to said area to be stitched by means of a needle carrier,
positioning said needle to enable a stitch to be set in said tissue by rotation of said needle about a first axis through mechanical manipulation of the needle carrier,
setting said stitch in said tissue by rotating said needle about a second axis, perpendicular to said first axis through mechanical manipulation of the needle carrier,
releasing and disengaging said needle from said needle carrier,
withdrawing said needle carrier from said cannula,
withdrawing said needle from said cannula by means of an instrument other than said needle carrier, and
tying knots to complete said stitch.

10. The method of claim 9 wherein said cannula is inserted through a puncture wound in the skin of said patient.

11. The method of suturing in a restricted field of surgical operation from an area of manipulation remote from said field which includes,
mechanically journaling from outside the area of limited accessibility a surgical needle for rotation on a first axis of rotation intersecting the field and the area,
mechanically journaling from outside the area of limited accessibility said surgical needle for rotation on a second axis of rotation perpendicular to said first axis.

12. Means for suturing in a restricted field of surgical operation from an area of manipulation remote from said field, comprising:
means including a first member supported for rotation on a first axis of rotation intersecting the field and the area,
means including a second member continuously axially adjustable relative to said first member parallel to said first axis,
means journaling said first member for rotation on a second axis of rotation perpendicular to said first axis,
an actuating means between said first and second members for effecting rotation on said second axis in response to relative axial adjustment of said second member.

13. The method of suturing in a restricted access zone which include the steps of
inserting an open ended hollow cannula into a restricted surgical access zone to form a pasasge extending from a manipulation area outside of the access zone into the access zone,
thereafter introducing into the access zone telescopically nested first and second members having means outside said access zone for manipulating a surgical needle rotationally about two axes inside said access zone.

* * * * *